US00PP26586P3

(12) United States Plant Patent
van der Sar

(10) Patent No.: US PP26,586 P3
(45) Date of Patent: Apr. 5, 2016

(54) *DIGITALIS* PLANT NAMED 'TAKFOPLGO'

(50) Latin Name: *Digitalis×hybrida*
Varietal Denomination: Takfoplgo

(71) Applicant: Takii Europe B.V., De Kwakel (NL)

(72) Inventor: Maarten van der Sar, Maasland (NL)

(73) Assignee: Takii Europe B.V., De Kwakel (NL)

( * ) Notice: Subject to any disclaimer, the term of this patent is extended or adjusted under 35 U.S.C. 154(b) by 87 days.

(21) Appl. No.: 14/121,363

(22) Filed: Aug. 25, 2014

(65) Prior Publication Data

US 2016/0057906 P1 Feb. 25, 2016

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Annette Para
(74) *Attorney, Agent, or Firm* — Audrey Charles

(57) ABSTRACT

A new and distinct cultivar of *Digitalis* plant named 'Takfoplgo', characterized by its plum-colored flowers, dark green-colored foliage, and moderately vigorous, columnar-upright growth habit, is disclosed.

1 Drawing Sheet

Latin name of genus and species of plant claimed: *Digitalis×hybrida.*

Variety denomination: 'Takfoplgo'.

BACKGROUND OF THE INVENTION

The present invention relates to a new and distinct cultivar of *Digitalis* plant botanically known as *Digitalis×hybrida* and hereinafter referred to by the cultivar name 'Takfoplgo'.

The new cultivar originated in a controlled breeding program in Honselersdijk, The Netherlands during June 2008. The objective of the breeding program was the development of *Digitalis* cultivars having unique flower coloration.

The new *Digitalis* cultivar is the result of cross-pollination. The female (seed) parent of the new cultivar is the proprietary *Digitalis purpurea* breeding selection coded 8044-1, not patented, characterized by its purple-colored flowers, dark green-colored foliage, and moderately vigorous, upright growth habit. The male (pollen) parent of the new cultivar is the proprietary *Digitalis canariensis* breeding selection coded 7738, not patented, characterized by its orange-colored flowers, dark green-colored foliage, and moderately vigorous, upright growth habit. The new cultivar was discovered and selected as a single flowering plant within the progeny of the above stated cross-pollination during June 2009 in a controlled environment in Honselersdijk, The Netherlands.

Asexual reproduction of the new cultivar by terminal stem cuttings since June 2009 in Honselersdijk, The Netherlands and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Takfoplgo' as a new and distinct cultivar of *Digitalis* plant:

1. Plum-colored flowers;
2. Dark green-colored foliage; and
3. Moderately vigorous, columnar-upright growth habit.

Plants of the new cultivar differ from plants of the female parent primarily in flower color and in having a smaller flower size. Plants of the new cultivar differ from plants of the male parent primarily in flower color and in having a larger flower size.

Of the many commercially available *Digitalis* cultivars, the most similar in comparison to the new cultivar is 'Illumination Flame', not patented. However, in comparison, plants of the new cultivar differ from plants of 'Illumination Flame' in at least the following characteristics:

1. Plants of the new cultivar has a darker flower color than plants of 'Illumination Flame'; and
2. Plants of the new cultivar are shorter than plants of 'Illumination Flame'.

In addition the new cultivar can be compared to Foxlight Ruby Glow 'Takforugl', U.S. Plant patent application Ser. No. 13/998,085. However, in comparison, plants of the new cultivar differ from plants of 'Takforugl' in having a darker flower color.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Takfoplgo'. The plants were grown in 1.5 gallon containers for approximately two months in a greenhouse and 12 weeks outdoors in West Chicago, Ill.

DETAILED BOTANICAL DESCRIPTION

Figure 1:
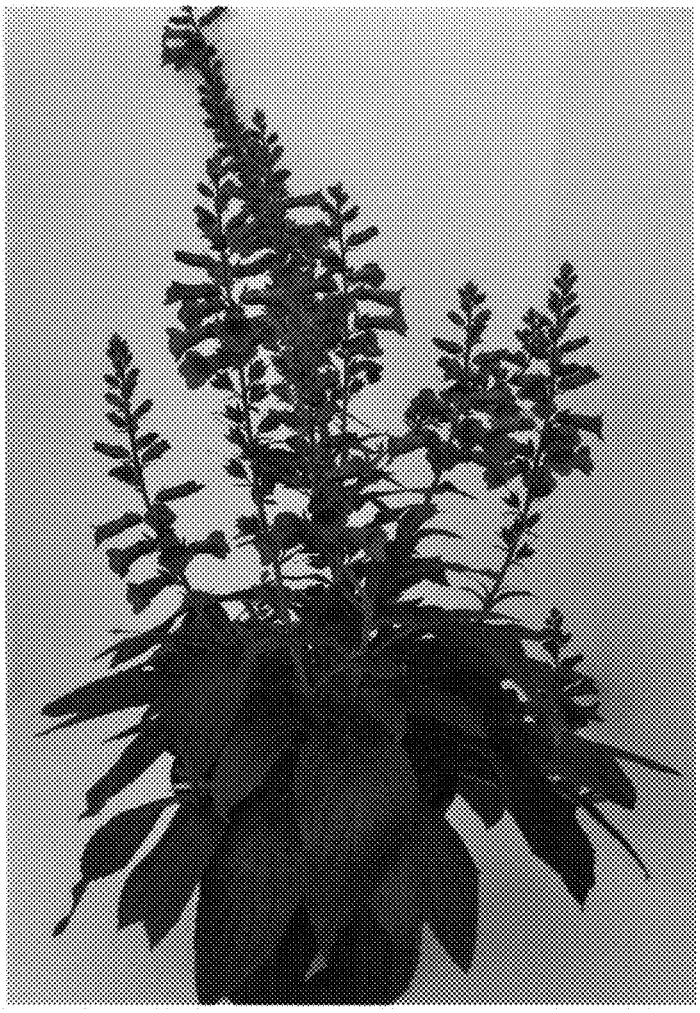
FIG. 1 illustrates a side view of the overall growth and flowering habit of 'Takfoplgo'.
Figure 2:
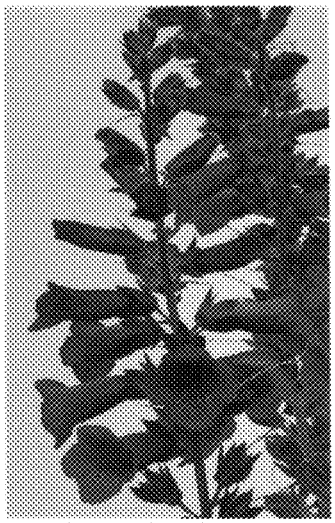
FIG. 2 illustrates a close-up view of an individual inflorescence of 'Takfoplgo'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in July 2014 under natural light conditions in West Chicago, Ill.

The following descriptions and measurements describe plants produced from cuttings from stock plants and grown under conditions comparable to those used in commercial practice. The plants were grown in 1.5 gallon containers for approximately two months in a greenhouse and 12 weeks outdoors in West Chicago, Ill. Greenhouse temperatures were maintained at approximately 45° F. to 65° F. (7.2° C. to 18.3° C.) during the day and approximately 35° F. to 45° F. (1.7° C. to 7.2° C.) during the night. No supplemental lighting was provided. Measurements and numerical values represent averages of typical plants.

Botanical classification: *Digitalis×hybrida* cultivar Takfoplgo.

Parentage:

*Female parent*.—Proprietary *Digitalis purpurea* breeding selection coded 8044-1, not patented.

*Male parent*.—Proprietary *Digitalis canariensis* breeding selection coded 7738, not patented.

Propagation:

*Type cutting*.—Terminal stem.

*Time to initiate roots*.—Approximately 15 to 20 days.

*Time to produce a rooted cutting*.—Approximately 42 to 49 days.

*Root description*.—Fine, fibrous.

*Rooting habit*.—Freely branching.

Plant description:

*Commercial crop time*.—Approximately 12 to 14 weeks from a rooted cutting to finish in a 15 cm pot.

*Growth habit and general appearance*.—Moderately vigorous, columnar-upright.

*Size*.—Height from soil level to top of plant plane: Approximately 68.0 cm. Width: Approximately 45.0 cm.

*Branching habit*.—Freely branching. Quantity of branches per plant: Approximately 1 main branch, with approximately 4 basal clumps.

*Main branch*.—Strength: Strong. Aspect: Erect. Length to base of inflorescence: Approximately 21.0 cm. Diameter: Approximately 1.3 cm. Length of central internode: Approximately 1.5 cm. Texture: Densely glandular pubescent. Gland color: Colorless, transparent. Color of young stem: 144A with an overlay of 187A. Color of mature stem: 144B to 144A with an overlay of 187A.

Foliage description:

*General description*.—Quantity of leaves per main branch: Approximately 30. Fragrance: None. Form: Simple. Arrangement: Rosette at plant base and alternate on flowering stems.

*Leaves*.—Aspect: Perpendicular or obtuse angle to stem. Shape: Elliptic to narrow elliptic. Margin: Serrate. Apex: Acute. Base: Attenuate. Venation pattern: Pinnate. Length of mature leaf: Approximately 20.0 cm. Width of mature leaf: Approximately 8.5 cm. Texture of upper and lower surfaces: Rugous, densely pubescent. Color of upper surface of young and mature foliage: N137A with venation of 146C. Color of lower surface of young and mature foliage: Closest to 138B with venation of 146D and midvein of 145D.

*Petiole*.—Length: Approximately 7.0 cm. Diameter: Approximately 1.7 cm. Texture: Densely pubescent. Color: Upper surface closest to 146D and lower surface closest to 145D.

Flowering description:

*Flowering habit*.—'Takfoplgo' is freely flowering under outdoor growing conditions with substantially continuous blooming throughout the summer.

*Lastingness of individual flower on the plant*.—Approximately 10 days.

Inflorescence description:

*General description*.—Type: Terminal raceme. Aspect: Primarily erect. Quantity per plant: Approximately 7. Fragrance: None. Length or height: Approximately 38.0 cm. Width: Approximately 10.0 cm. Quantity of fully open flowers per inflorescence: Approximately 8.

*Peduncle*.—Strength: Strong. Aspect: Erect. Length: Approximately 14.5 cm. Diameter: Approximately 5.0 mm to 8.0 mm. Texture: Densely glandular pubescent. Gland color: Colorless, transparent. Color: 144B to 144A tinted 187A in sun.

Flower description:

*Type*.—Single, campanulate, not persistent.

*Bud just before opening*.—Shape: Ovoid. Length: Approximately 1.5 cm. Diameter: Approximately 7.0 mm. Color: Calyx of 146B with an overlay of 187A, petal portion N79B.

*Corolla*.—Shape: Bilabiate. Aspect: Facing outward and downward. Length: Approximately 2.8 cm. Width: Approximately 3.0 cm. Depth: Approximately 4.3 cm.

*Petals*.—Quantity: 5 petals fused at base forming a throat and consisting of an upper lip with three lobes and a single-lobed projecting lower lip. Shape: Obovate. Margin: Entire, ciliate. Apex: Obtuse, with lateral lobes slightly notched.

*Upper lip*.—Length of upper lobe from throat: Approximately 7.0 mm. Width of upper lobe: Approximately 1.9 cm. Length of lateral lobes from throat: Approximately 7.0 mm. Width of lateral lobes: Approximately 1.2 cm. Texture of upper (inner) surface: Glabrous. Texture of lower (outer) surface: Densely glandular pubescent. Gland color: Colorless, transparent. Color of upper surface when fully open: N79D. Color of lower surface when fully open: N79C.

*Lower lip*.—Length of lobe from throat: Approximately 1.0 cm. Width: Approximately 1.8 cm. Texture of upper (inner) surface: Moderately pubescent. Texture of lower (outer) surface: Densely glandular pubescent. Gland color: Colorless, transparent. Color of upper surface when fully open: Margin of N79D with central nectar glide approximately 3.0 mm from margin; glide has base color of NN155A with an overlay of N79D, spots throughout of 187A, and side borders of 168B. Color of lower surface when fully open: N79D.

*Corolla tube*.—Length: Approximately 3.5 cm. Width: Approximately 1.8 cm. Texture of inner surface: Sparsely pubescent on lower portion (nectar glide). Texture of outer surface: Glabrous. Color of inner surface: N79D with nectar glide continuing from lower lip; glide has base color of NN155A with an overlay of N79D, spots throughout of 187A, and side borders of 168B. Color of outer surface: N79C and lower portion of N79D with irregular spots of NN155D.

*Calyx*.—Shape: Cupped, tips flare out with age. Diameter: Approximately 2.0 cm.

*Sepals*.—Quantity per flower: 5. Shape: Lanceolate. Apex: Acute. Base: Truncate. Length: Approximately 1.5 cm. Width: Approximately 8.0 mm. Texture of upper and lower surfaces: Densely pubescent. Color of upper (inner) and lower (outer) surfaces: 137A, apex tinted 187A in sun.

*Pedicel*.—Strength: Strong. Aspect: Acute angle to stem. Length: Approximately 7.0 mm. Diameter: Approximately 1.0 mm. Texture: Densely glandular pubescent. Gland color: Colorless, transparent. Color: 144A tinted 187A in sun.

*Reproductive organs*.—Androecium: Stamen quantity: 4, basifixed. Stamen length: Approximately 2.8 cm. Filament length of fixed portion: Approximately 1.2 cm. Filament color: N79C. Anther shape: Reniform. Anther length: Approximately 3.0 mm. Anther color: 7A. Pollen amount: Abundant. Pollen color: 155D. Gynoecium: Pistil quantity: 1 per flower. Pistil length: Approximately 3.0 cm. Stigma shape: Bifid. Stigma length: Approximately 1.0 mm. Stigma color: 155D. Style length: Approximately 1.9 cm. Style color: 145D with an overlay of N79D, overlay heavy near stigma. Ovary length: Approximately 1.0 cm. Ovary texture: Densely pubescent. Ovary color: 144B.

Seed and fruit production: Neither seed nor fruit production has been observed.

Disease and pest resistance: Resistance to pathogens and pests common to *Digitalis* has not been observed.

What is claimed is:

1. A new and distinct cultivar of *Digitalis* plant named 'Takfoplgo', substantially as herein shown and described.

* * * * *